United States Patent [19]

North

[11] 4,327,588

[45] May 4, 1982

[54] AUTO-RANGING ULTRASONIC ATTENUATION METERS

[75] Inventor: Desmond J. North, Brackley, England

[73] Assignee: The Secretary of State for Defence in Her Britannic Majesty's Government of the United Kingdom of Great Britain and Northern Ireland, London, England

[21] Appl. No.: 182,247

[22] Filed: Aug. 28, 1980

[51] Int. Cl.[3] .............................................. G01N 29/04
[52] U.S. Cl. .......................................... 73/599; 73/602
[58] Field of Search .................................. 73/599, 60 L

[56] References Cited

U.S. PATENT DOCUMENTS

4,105,018  8/1978  Greenleaf et al. .................. 73/602
4,202,215  5/1980  Meyer .................................. 73/599

*Primary Examiner*—Anthony V. Ciarlante
*Attorney, Agent, or Firm*—Nathan Edelberg; Jeremiah G. Murray; Edward Goldberg

[57] ABSTRACT

An ultrasonic flaw detection system automatically measures attenuation of an input signal from a receiver transducer that provides a reference level. Successive amplifier stages having stepped gains provide graduated output levels that are detected and stored by individual peak readers. Sampled output levels are compared in comparators and with a reference voltage generated by a digital-to-analog converter to produce a binary output corresponding to each signal as a first coarse attenuation level. Logic control and timing circuitry selects the output level corresponding to one of the signals having a peak voltage in a predetermined range. A logarithmic converter and comparator provide a fine attenuation reading which is summed with the coarse reading in digital form. This is decoded and displayed as a total attenuation readout.

6 Claims, 14 Drawing Figures

AUTO-RANGING ULTRASONIC ATTENUATION METERS

BACKGROUND OF THE INVENTION

1. Field of the Invention

The present invention relates to auto-ranging ultrasonic attenuation meters such as may be used for detecting voids, inclusions, cracks or other flaws in, for example, solid propellant rocket motors.

2. Description of the Prior Art

One method which has been employed to measure the attenuation of an ultrasonic signal involves the measurement of the amplitude of the attenuated signal waveform on a cathode ray tube (CRT) display. A test specimen is placed between an ultrasonic transmitter and receiver, and the transmitter energized by electrical pulses of 1 μs duration. The receiver output is fed via an emitter follower, attenuator and tuned amplifiers to an input of an ultrasonic test set which has a CRT display. By adjustment of the attenuator and X and Y axis controls of the CRT, the amplitude of the waveform of the input can be measured and compared with the amplitude of the transmitter output signal. One disadvantage of such a method is that the dynamic measurement range is low. In one particular system the dynamic range was 14 decibels (dB) and was only obtained by a continuous manipulation of the system controls.

In a second known method a similar arrangement of emitter follower, attenuator and tuned amplifiers is used but the results are presented as an array of dots produced by a printer instead of a waveform on a CRT display. The number of dots printed is proportional to the amplitude of the received signal. The printing speed of dot printer, which is typically 120 dots per second, imposes a limit on the pulse repetition frequency (prf) of the ultrasonic signal which may be used.

SUMMARY OF THE INVENTION

The present invention provides an ultrasonic attenuation meter having a large dynamic range and capable of operation at high prf levels.

According to the present invention an auto-ranging ultrasonic attenuation meter includes a multistage amplifier for producing amplified signals from an input signal from an ultrasonic receiver transducer, amplitude reader means for determining the peak amplitude of the input signal and the amplified signals, comparator means for comparing the peak voltage of the signals with a reference voltage and to produce a binary output corresponding to each of said signals as a first quantization of attenuation level, selection means for selecting from said outputs an output corresponding to the one of said signals having a peak voltage in a predetermined range, and comparison means for comparing the voltage of the selected output with a ramp voltage as a second quantization of attenuation level. The first and second quantizations may be summed while in digital form, decoded and displayed as a digital readout.

Embodiments of the invention will now be described by way of example only with reference to the accompanying drawings of which:

DESCRIPTION OF THE PREFERRED EMBODIMENT

As an ultrasonic signal traverses a medium, energy is extracted from it, reducing its intensity. The change of intensity ΔI as expressed in decibels (dB) is given by:

$$\Delta I = 10 \log_{10}(I_2/I_1) \text{dB} \tag{1}$$

(see for example "Fundamentals of Ultrasonics" by Blitz, J., published by Butterworth 1967) where $I_1$ and $I_2$ represent the initial and final intensities, respectively, of the ultrasonic pulse. It can also be shown that:

$$I \propto A^2 \tag{2}$$

where A is the amplitude of a beam of intensity I. If $A_1$ and $A_2$ are the amplitudes corresponding to intensities $I_1$ and $I_2$ respectively, the change in amplitude ΔA is given by:

$$\Delta A = 20 \log_{10}(A_2/A_1) \text{dB}. \tag{3}$$

The attenuation meter in accordance with the invention measures the amplitude level $A_2$. $A_1$ is chosen to be +10 V. As attenuation measurements are made relative to a selected level and the system is calibrated, $A_1$ may be chosen arbitrarily. The input amplitude to a transmitting probe (not shown) must remain constant (within ±2%).

From equation (3) it can be shown that if the ratio $A_2/A_1$ is 1, 1/10, 1/100, ... $1/10^n$ the corresponding amplitude level change in dB is 0, −20 dB, −40 dB ... −20 n dB where $n = 0, 1, 2, 3 \ldots$ etc.

In accordance with an embodiment of the invention an input signal is amplified through successive stages in a cascade of amplifier stages each having a gain of, for example, 20 dB. The amplifier stage, the output of which is in the range +1 to +10 V peak, is located and selected for processing. Its position in the cascade immediately indicates the "coarse" range in which the input signal lies, i.e. 0-20, 20-40, 40-60 or 60-80 dB below the selected reference level. The "fine" range is obtained by processing that output logarithmically between +1 and +10 V peak, this being a convenient range for the circuit components. The result is a reading within a span of 0-20 dB to a resolution of 0.5 dB. Summation of the "coarse" and "fine" readings gives the total attenuation level, in dB, of the input signal.

Figure 1:
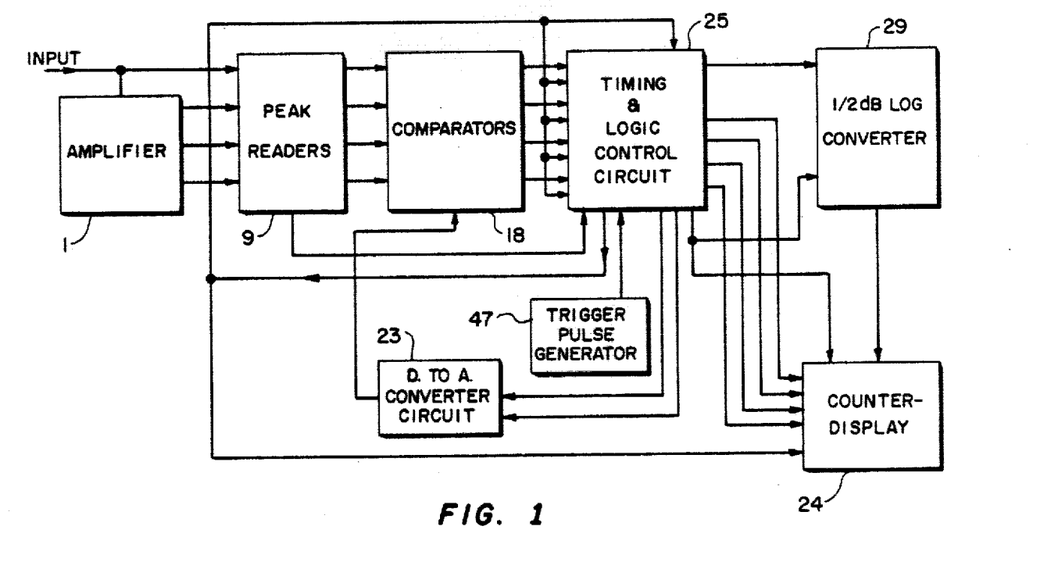
FIG. 1 shows a block diagram of the circuit of an auto-ranging ultrasonic attenuation meter in accordance with the invention.
Figure 2:
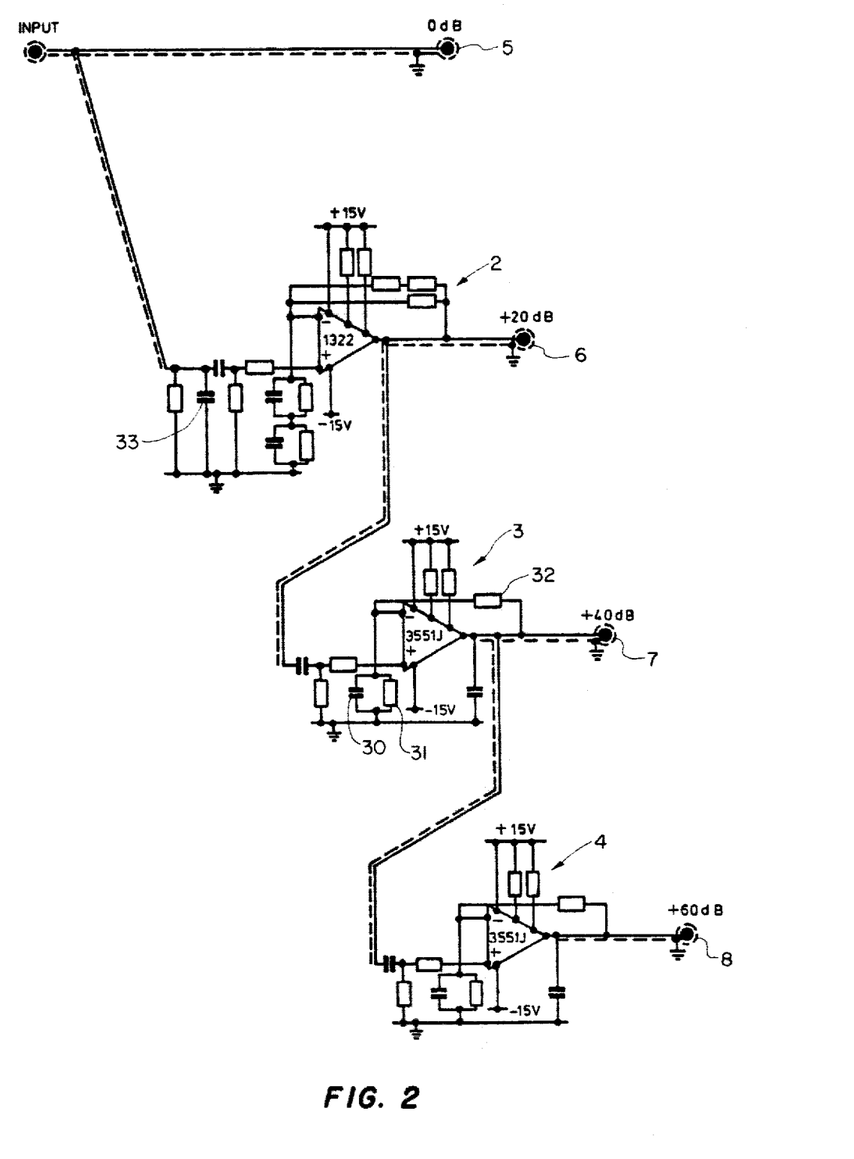
FIG. 2 shows a circuit diagram of an amplifier which forms part of the circuit of FIG. 1.
Figure 14:
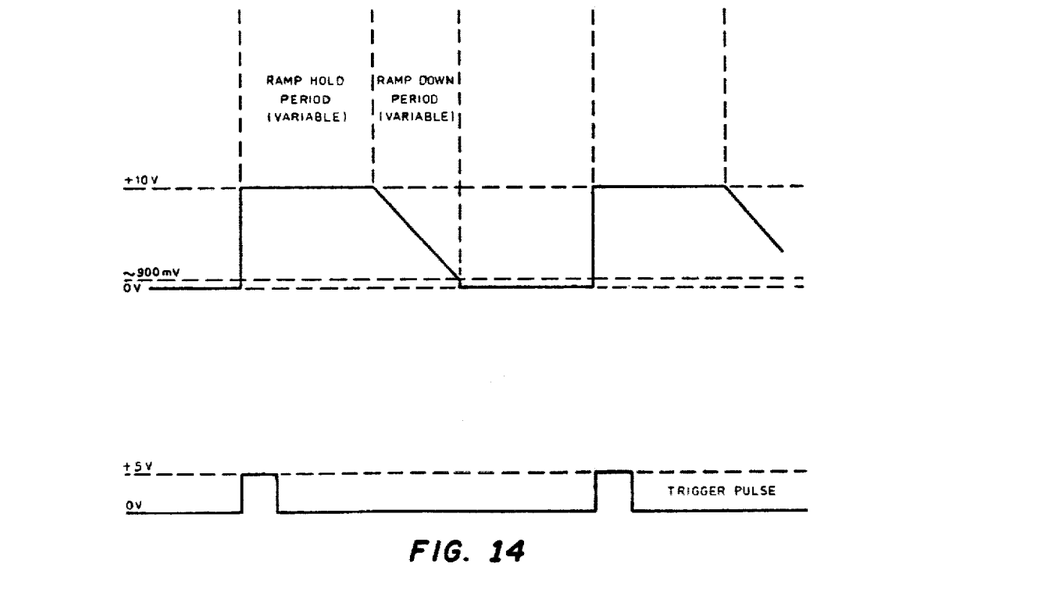
FIG. 14 is a diagram showing the form of a comparator reference ramp voltage.

Referring to FIGS. 1 and 2, a signal from an ultrasonic receiver transducer (not shown) is amplified through a three stage amplifier 1, which is shown in detail in FIG. 2. The stages of the amplifier 2, 3 and 4 are each of 20 dB gain and provide outputs on lines 6, 7 and 8 at 20, 40 and 60 dB, respectively, above the input level of 0 dB which is supplied on a line 5. The output signals are detected and stored by a set of peak readers 9, which is shown in detail in FIG. 3 in which input lines 10, 11, 12 and 13 connected to lines 5, 6, 7, 8 respectively, feed peak readers 14, 15, 16 and 17. Sampled levels are compared in a set of comparators 18, which is shown in detail in FIG. 4, in which four comparators 19, 20, 21 and 22 receive signals from the peak readers. A comparator reference ramp-voltage signal, of the form shown in FIG. 14, is generated by a digital-to-analog converter (DAC) 23, which is shown in detail in FIG. 7, and the sampled levels are compared with the ramp voltage.

During a ramp holding period, i.e. when the ramp level is steady at +10 V, "coarse" attenuation levels are read. For a peak level of +10 V, or more, at input, the comparator gives a logical '1' (high) output and 0 dB is added to a counter-display 24, shown in more detail in FIG. 9. For an input of less than +10 V, the comparators 18 gives a logical '0' output (low). A 20 dB step is added to the display 24 for each '0' level output. Data is clocked to, and held at, the display stage.

A timing and logic control circuit 25 selects the first comparator in the chain, the output of which is at '0'. A high frequency clock drive 26, 100 kHz to 1 MHz, which forms part of the timing and logic control circuit 25, is fed simultaneously to the DAC 23 and to an eight-bit binary counter 28a-28h, which forms part of a ½ dB log converter 29, the input to which is gated by the comparator output. The ramp voltage is driven down by the clock, and when this level becomes equal to the comparator input level, the comparator output changes state and inhibits the clock drive to the counter 28. The complements of the binary data produced by the counter are directly proportional to the input voltage.

The eight-bit data generated by the counter 28 are processed in the ½ dB logarithmic converter. The output of the converter 29 is a six-bit word which is the binary logarithm of the eight-bit data over a range of 20 dB to a resolution of ½ dB. This gives the "fine" attenuation reading.

Figure 9:
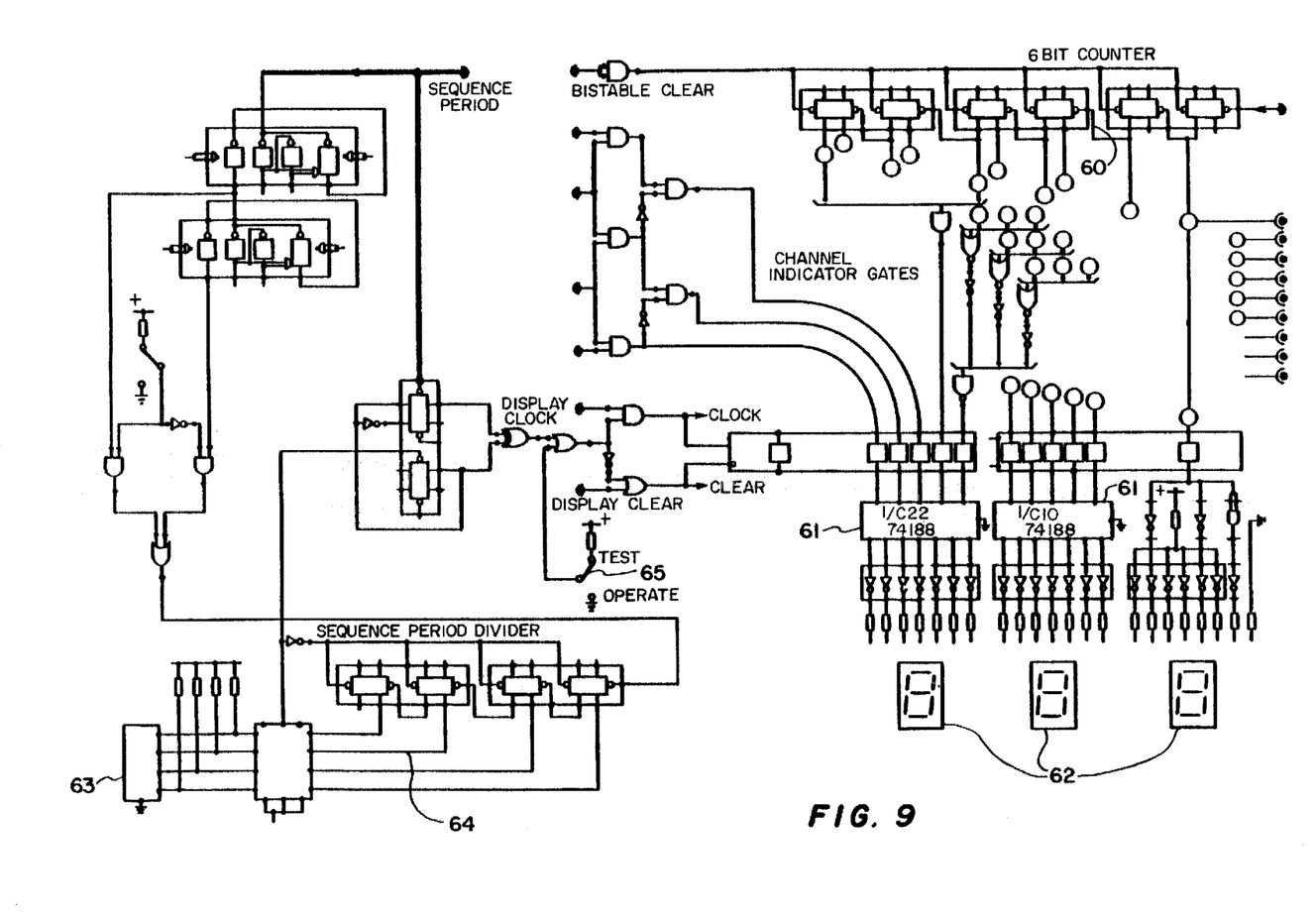
FIG. 9 shows a circuit diagram of a counter-display circuit which also forms part of the circuit of FIG. 1.

The "coarse" and "fine" readings are summed while in digital form and decoded to give a seven-segment numerical display, shown in detail in FIG. 9. The total attenuation is then displayed directly in dB.

Referring to FIG. 2, the amplifier uses standard, integrated circuit operational amplifiers, selected for their high slew rate, large output voltage swing, wide full-power bandwidth, low noise and low voltage drift characteristics. The three cascaded stages 2, 3 and 4 are operated in the non-inverting mode for high input impedance, and are a.c. coupled to minimize d.c. offsets. Each stage is required to give a gain of 20 dB ($\times 10$) so that overall gains of 0, 20, 40 and 60 dB ($\pm 0.5$ dB) can be obtained over a frequency range of 60 kHz to 500 kHz. To provide extra lift in the response at high frequencies, giving a flat characteristic with no roll-off to 500 kHz, gain compensation is employed.

The closed-loop voltage gain $A_{VCL}$ of an operational amplifier, in the non-inverting mode, is given by $$A_{VCL}=1+(R_f/R_i)$$

for large values of open-loop gain, where $R_f$ is a feedback resistor 32 in amplifier 3 connecting the output to the inverting input, and $R_i$ is a resistor 31 connecting the inverting input to ground.

If $R_i$ is reduced at high frequencies, $A_{VCL}$ increases and counteracts the output roll-off of the amplifier. To achieve this effect a small compensation capacitor $C_c$, 30, of about 100 pF, is connected across $R_i$ so that the parallel impedance of $R_i$ with $C_c$ decreases with increasing frequency, thereby increasing $A_{VCL}$. The values of the capacitors can be calculated to a reasonable degree of accuracy.

Figure 10:
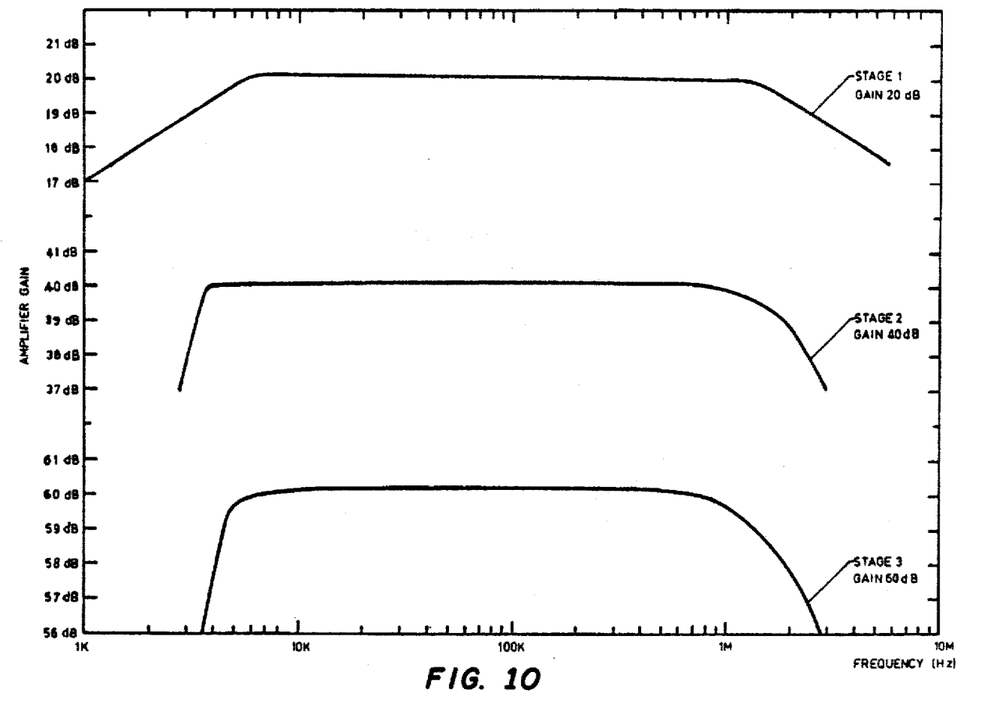
FIG. 10 is a graph showing the frequency response curves of the amplifier of FIG. 2.

Tests have shown that the amplifier has a frequency response from 5 kHz to 1 MHz (see FIG. 10), within the required gain limits, when driven from a 75 ohm source.

The input impedance of the amplifier is about 3 k ohms at 100 kHz, falling to 750 ohms at 1 MHz. A 220 pf capacitor, 33, is connected across the input to reduce unwanted high frequency signals.

Measurements have shown the input noise to be about 70 $\mu$V rms over the operating frequency range.

Figure 3:
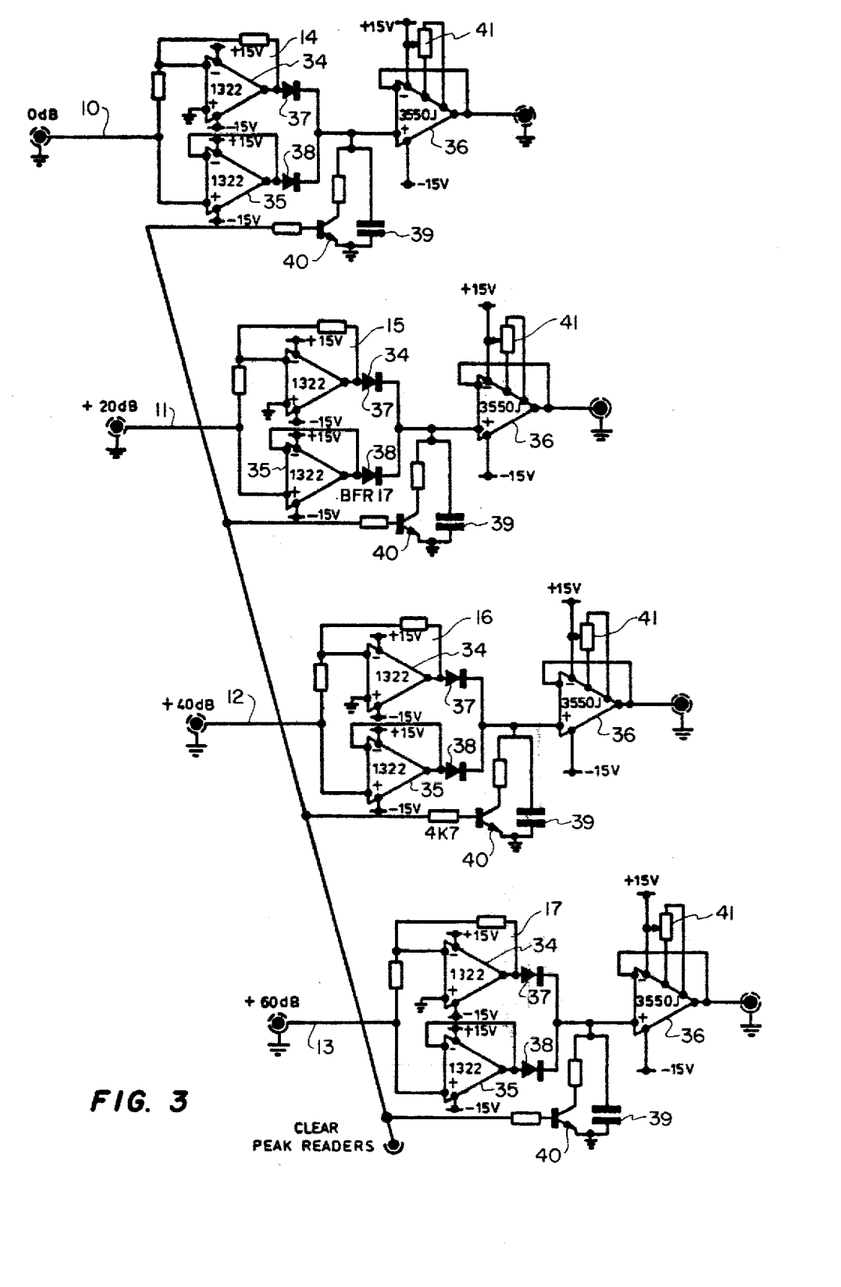
FIG. 3 shows a circuit diagram of a set of four peak readers which forms part of the circuit of FIG. 1.

Referring to FIG. 3, each of the peak readers 14, 15, 16 and 17 uses three integrated circuit operational amplifiers 34, 35 and 36. Input signals to each peak reader are processed through both inverting and non-inverting unity gain followers and the outputs of each are driven through type 1S120 diodes 37, 38 to a storage capacitor 39. This method effectively doubles the charging current to the storage capacitor 39 since it is being positively charged from both halves of the input waveform. The storage capacitor 39 can be charged to within $v_d$ of the peak input signal, where $v_d$ is the forward voltage drop across one diode. The diodes 37, 38 prevent charge leaking back through the outputs of the input stages. The third operational amplifier 36 has very high input impedance, of the order of $10^{11}$ ohms in parallel with 3 pf, to buffer the storage capacitor 39, permitting long storage times.

A transistor 40, connected across the capacitor 39 to perform the 'reset' function, is turned 'on' by a delay pulse, dissipating the stored charge and zeroing a buffer input. This function is performed within 2 $\mu$s.

The output stage features a variable 25 k ohms resistor 41, termed 'offset control'. This is used to set the peak reader output to +1 V for a +1 V peak input, enabling the operation to be carried out within the required accuracy limits ($\pm 0.5$ dB of the input level) for input voltages in the range +1 to +10 V peak.

Tests have shown that each peak reader has a dynamic range of 24 dB (+600 mV to +10 V peak at input) from DC to 1 MHz within the required limits of accuracy. The output droop rate of the readers has been measured as 30 mV in 5 ms, which is within acceptable limits.

Figure 4:
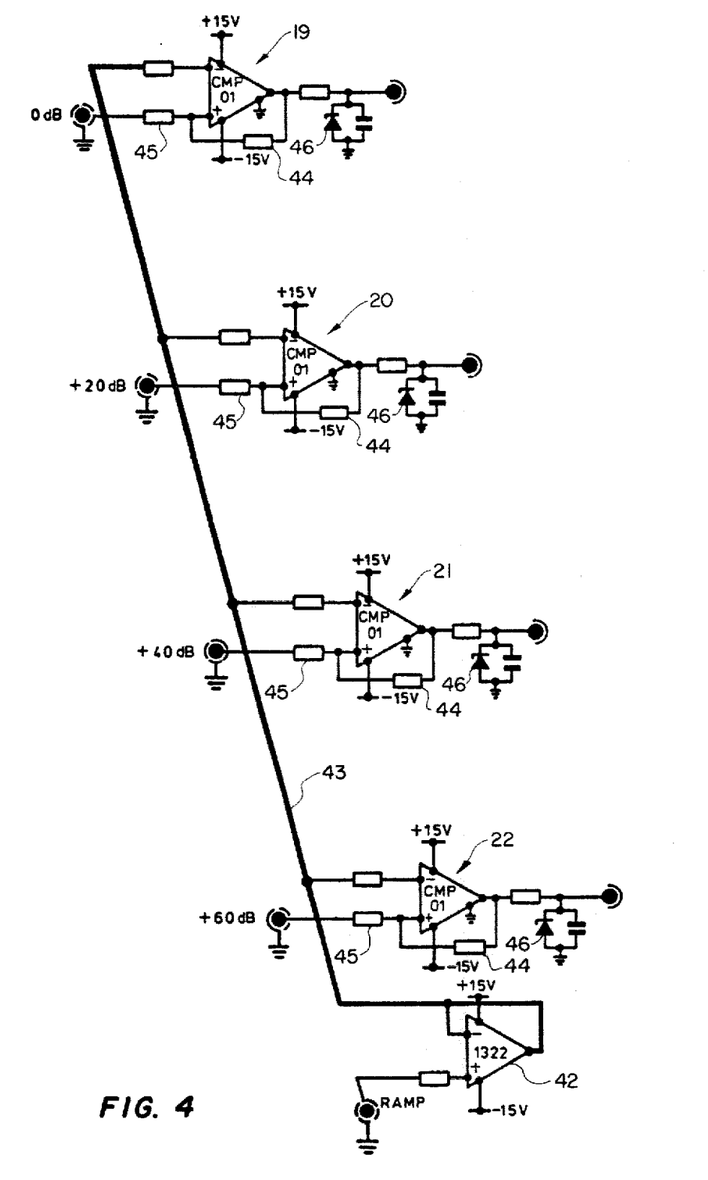
FIG. 4 shows a circuit diagram of a comparator which forms part of the circuit of FIG. 1.

The comparator circuit 18, shown in detail in FIG. 4, incorporates four high speed comparators 19, 20, 21 and 22 and a buffer 42 for the DAC output, as this is limited to 2 mA full scale, having high differential input impedance, fast response, large input slew rate and high open loop voltage gain ($A_{vol}$) and the power supplies are $\pm 15$ V.

Buffered reference ramp voltage is supplied via a line to all comparator inverting inputs. The sampled input levels are connected to the non-inverting inputs of the comparators. For input signals greater than the reference level, the comparator assumes a high output state, while for input signals less than the reference level, it assumes a low output state.

To increase the speed of the low-to-high transition in the comparator output, and to ensure one-shot operation of the comparators, positive feedback is applied. Each comparator output is connected through a high value resistor 44 to the non-inverting input, and the input voltage to the non-inverting input is driven via a resistor 45, to give the comparator a hysteretic output characteristic. The hysteresis width, a voltage, $V_H$, of each comparator, is given by:

$$V_H \leq R_i/(R_i+R_f) \times 4 \text{ volts}$$

where $R_f$ is the resistance of resistors 44 and $R_i$ is the resistance of resistors 45.

Each comparator output is clamped by a 4.7 Zener diode 46 to ground so that the output levels generated are TTL-compatible.

Figure 5:
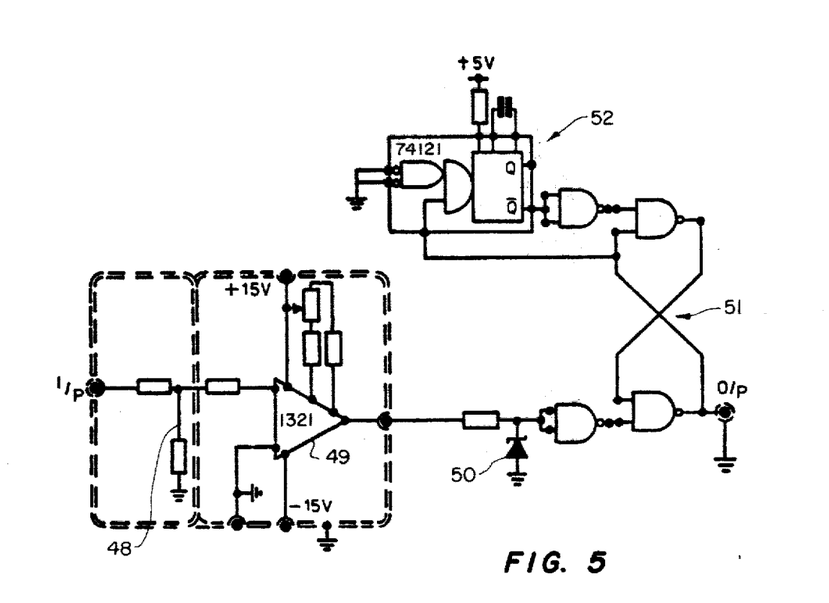
FIG. 5 shows a circuit diagram of a trigger pulse generator which forms part of the circuit of FIG. 1.
Figure 11:
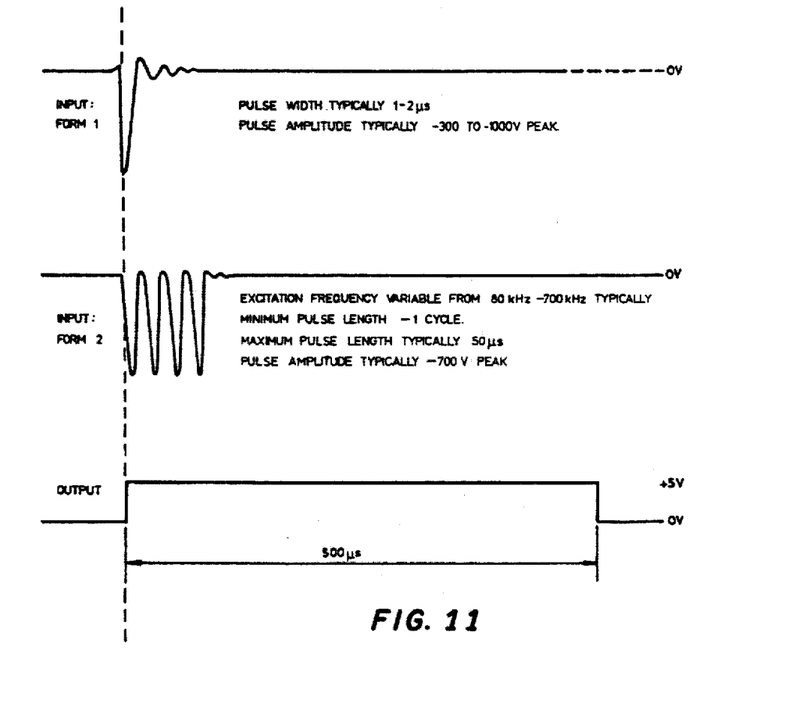
FIG. 11 is a diagram showing input and output states of the trigger pulse generator of FIG. 5.

A trigger pulse generator 47, shown in detail in FIG. 5, is designed to accept negative-going transmission pulses, in the range $-50$ V to $-1000$ V, and to generate a TTL-compatible output pulse of 500 $\mu$s duration, the positive-going edge of which coincides with the first negative-going transmission level, as shown in FIG. 11.

The generator has an input circuit which consists of a potential divider 48 driving the inverting input of an operational amplifier 49 having a value of $A_{vol}$ of the order of $10^5$, and acts as a zero-crossing detector. The output of the detector swings positive for negative-going input levels and negative for positive-going transitions. A 3.9 V Zener diode 50 provides a TTL-compatible output drive to a set-reset latch 51 which is reset by a monostable 52 after 500 $\mu$s.

Figure 6:
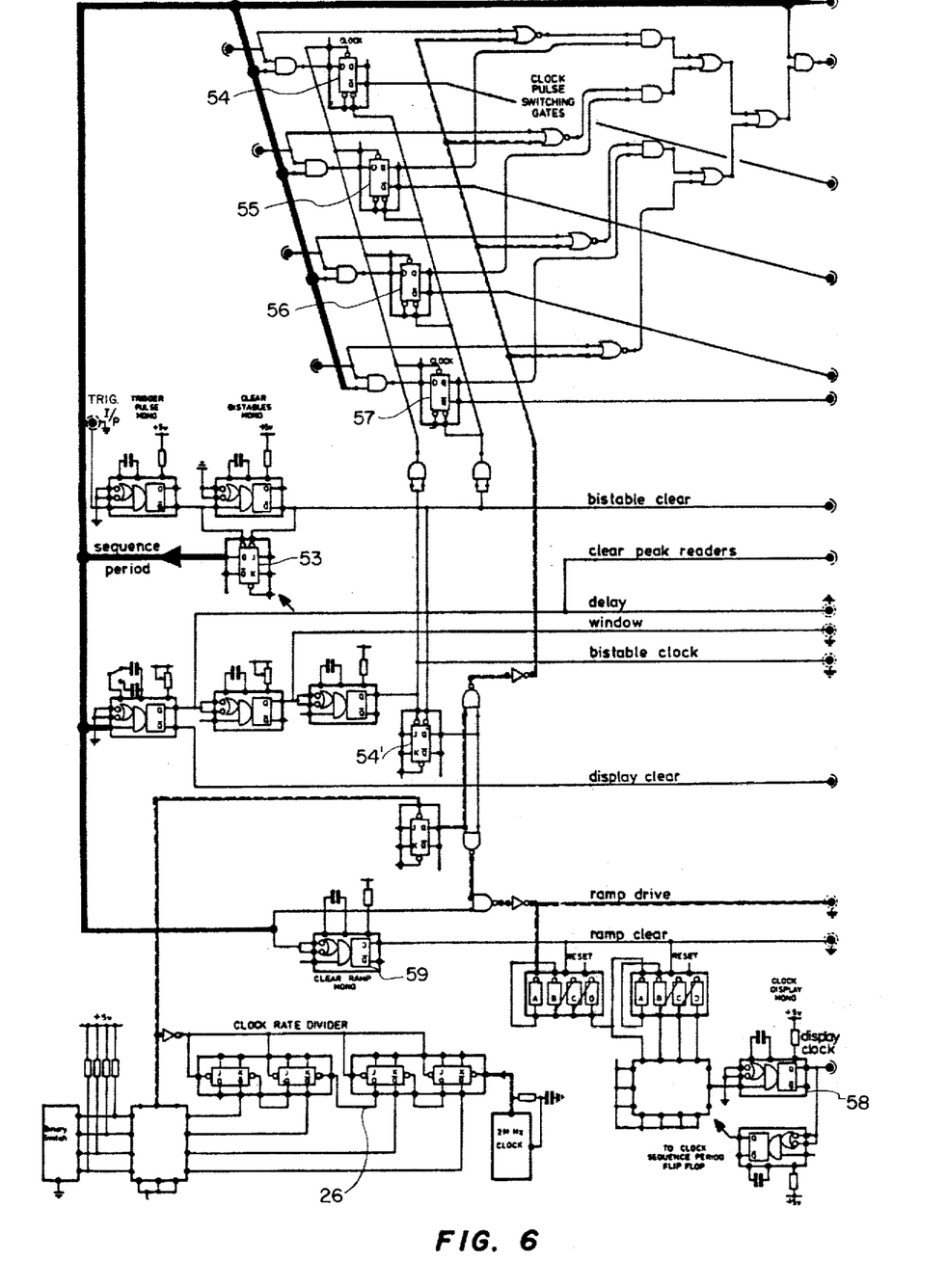
FIG. 6 shows a circuit diagram of a timing and logic control circuit which forms part of the circuit of FIG. 1.
Figure 12:
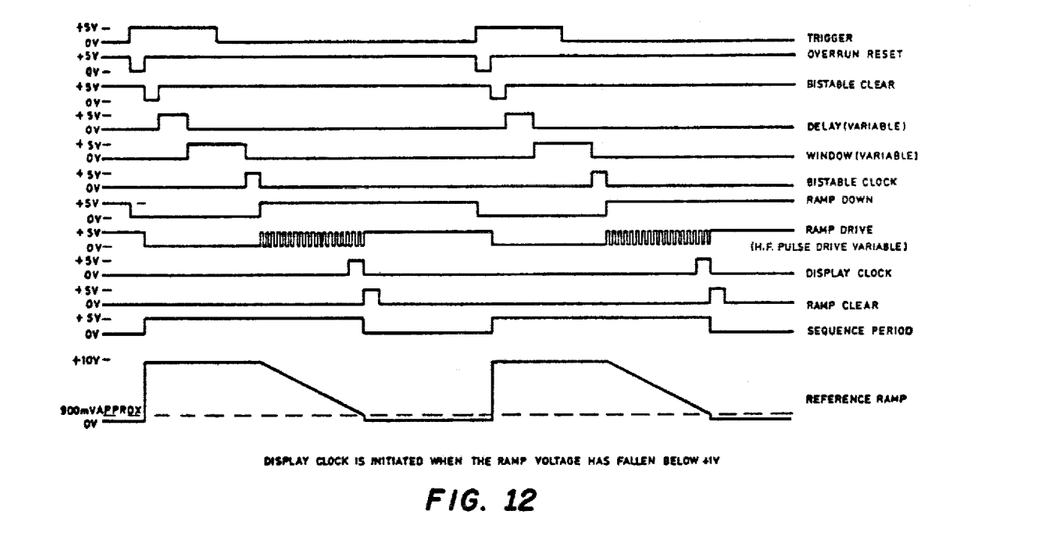
FIG. 12 is a diagram showing timing sequences of the timing and logic control circuit of FIG. 6.

The prime function of the timing and logic control circuit 25 shown in detail in FIG. 6 is to generate a timing sequence as shown in FIG. 12. The timing circuit operates as follows:

The positive edge of a trigger pulse from the generator 47 trips an 'overrun reset' which ensures that the 'Q' output of a bistable 53 is set to a logical '0'. This prevents the output from locking into a high state if successive processing periods overlap.

A bistable clear pulse sets all counter and flip-flop outputs to '0' but presets the 'Q' output of bistable 53 to a '1'.

A delay pulse is generated to set the peak-readers 14, 15, 16, 17 in the 'reset' mode, inhibiting the system and disregarding any transmission breakthrough into the amplifier. The pulse length of the delay pulse is variable over two ranges; from 1.30 $\mu$s to 76 $\mu$s and from 136 $\mu$s to 7.6 ms.

A window pulse is generated which opens a peak-reading period. The window pulse length is variable from 132 $\mu$s to 6.4 ms and is set so that it just encompasses the input pulse.

A bistable clock pulse 54' generates and locks the initial comparator output states, i.e. those set during the 'ramp-holding' period, into four delay bistables 54, 55, 56 and 57, for decoding and is retained until the next trigger period is initiated.

A ramp down period is initiated by the trailing edge of the bistable clock pulse, driving a high frequency pulse train to the DAC 23, generating a falling ramp voltage. The pulses are also driven to the $\frac{1}{2}$ dB logarithmic converter 29 so that both reference voltage and the logarithmic conversion function are generated to synchronism. The pulse drive to the $\frac{1}{2}$ dB logarithmic converter 29 is inhibited when the reference voltage has fallen to a level equal to the input level of whichever comparator has an input in the range $+1$ to $+10$ V peak.

The pulse drive to the DAC 23 is maintained until the output level has fallen to around 900 mV. A display clock 58 pulse clocks all decoded data to display stages on the counter display 24. The data is held until it is reset by the complement of delay pulse ($\overline{\text{delay-display}}$ clear) or bistable clear pulse.

A ramp clear pulse from a monostable 59 sets the DAC output to 0 V, completing the operating cycle. The cycle is repeated when the next trigger pulse is initiated.

A logic control function is performed by the four delay bistables 54, 55, 56 and 57 and associated 'AND', 'NOR' and 'OR' gates. The circuit 25 automatically selects, for fine processing, the input level to the first comparator in the chain whose output is at logical '0', i.e. the comparator, the input voltage of which is in the range $+1$ to $+10$ V peak.

The circuit 25 is designed to allow high frequency pulses through to the $\frac{1}{2}$ db logarithmic converter 29, until the reference voltage has fallen to the level of the input signal being processed, producing a change of output state in the corresponding comparator.

Figure 7:
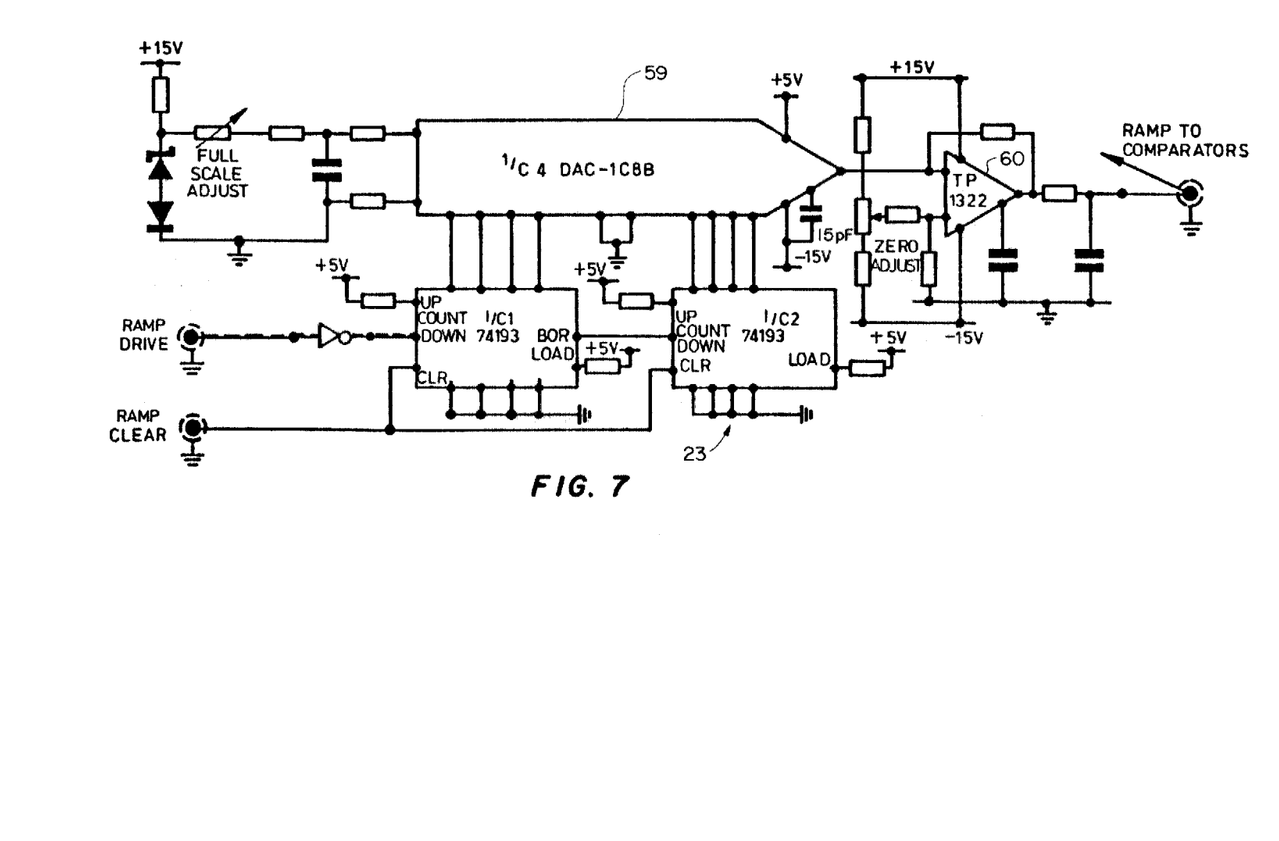
FIG. 7 shows a circuit diagram of a digital to analog converter, which forms part of the circuit of FIG. 1.

The DAC circuit 23 shown in FIG. 7 uses a 16-pin dual-in-line monolithic integrated DAC, 59, to perform a digital-to-analog conversion and requires that parallel input data and the serial data, from the ramp drive output, are converted to this form by an eight-bit up-down counter. Voltage output of circuit 23 is generated by an operational amplifier 60 incorporating both full scale and offset adjustments.

The circuit 23 is designed to operate in the 'backward' mode, the first pulse driving the output to full scale, ensuing pulses causing the 'ramp down' function to be generated.

Figure 8:
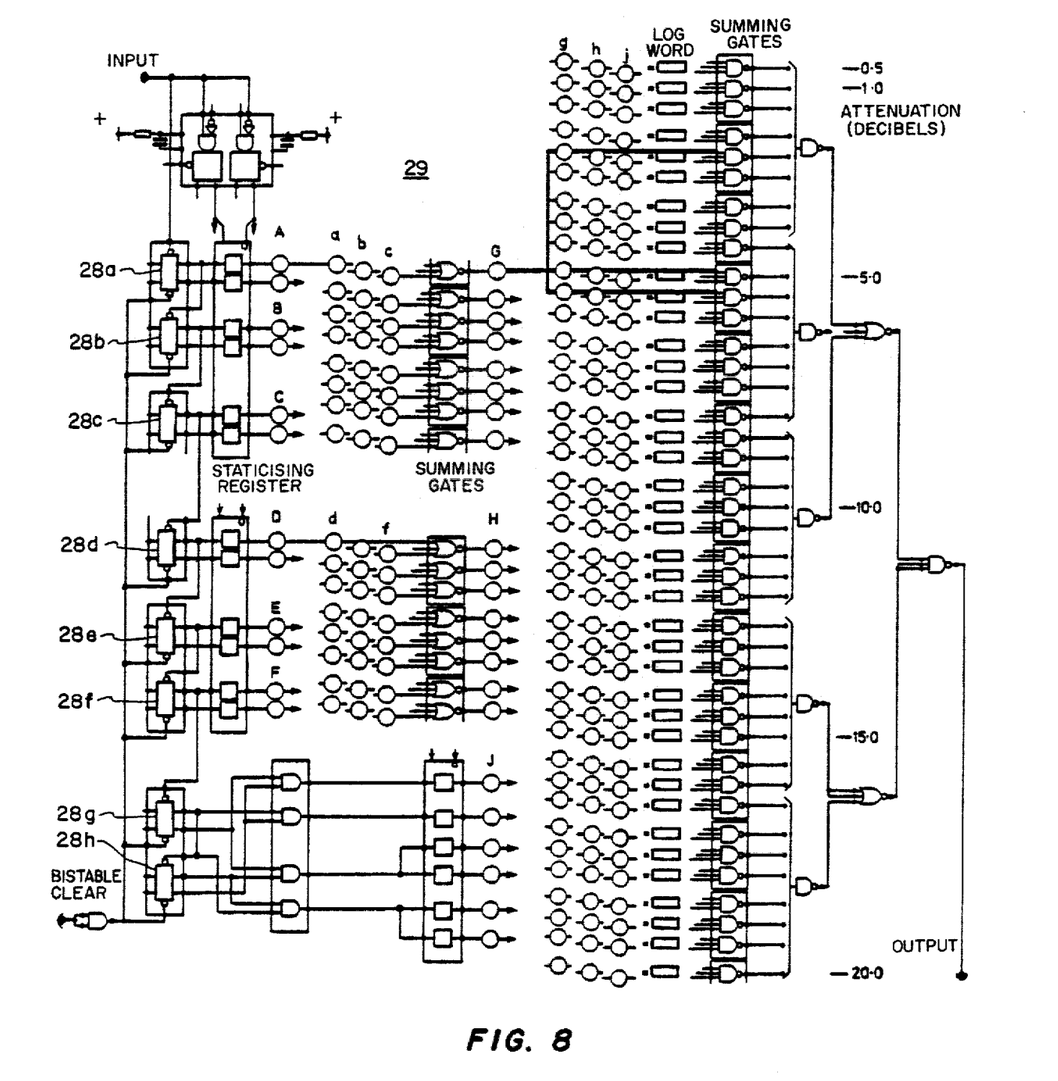
FIG. 8 shows a circuit diagram of a ½ dB log converter which forms part of the circuit of FIG. 1.

The $\frac{1}{2}$ dB logarithmic converter 29 shown in FIG. 8 is a decoder designed to produce one output pulse for each of a set of 40 words from 256 generated by the eight-bit counters 28. Pulse drive to the counters is provided by the timing and logic control circuit 25 and gated by the selected comparator output. The complement of the eight-bit word generated is directly proportional to the input voltage, a change of 1 least significant bit corresponding to a 40 mV step in the output, over a 20 dB range from $+1$ to $+10$ V peak. A logic network selects the word required to produce an output pulse. The output is in a logarithmic sequence so that, when driving a six-bit counter, it generates a binary word which is the logarithm of the eight-bit word. The converter covers a range of 20 dB with a resolution of $\frac{1}{2}$ dB. The sequence generated by the converter 29 is shown in Table 1.

TABLE 1

Sequence generated by ½ dB log converter

The ½ dB log converter generates an output pulse for each of the following binary input configurations. The attenuation corresponding to each input word is given.

| Input MSB LSB | Attenuation (dB) | Input MSB LSB | Attenuation (dB) |
|---|---|---|---|
| 0 0 0 0 0 0 0 0 | 0 | 1 0 1 0 1 1 1 0 | 10.0 |
| 0 0 0 0 1 1 1 0 | 0.5 | 1 0 1 1 0 0 1 1 | 10.5 |
| 0 0 0 1 1 1 0 0 | 1.0 | 1 0 1 1 0 1 1 1 | 11.0 |
| 0 0 1 0 1 0 0 1 | 1.5 | 1 0 1 1 1 0 1 1 | 11.5 |
| 0 0 1 1 0 1 0 1 | 2.0 | 1 0 1 1 1 1 1 1 | 12.0 |
| 0 1 0 0 0 0 0 0 | 2.5 | 1 1 0 0 0 0 1 0 | 12.5 |
| 0 1 0 0 1 0 1 0 | 3.0 | 1 1 0 0 0 1 1 0 | 13.0 |
| 0 1 0 1 0 1 0 1 | 3.5 | 1 1 0 0 1 0 0 1 | 13.5 |
| 0 1 0 1 1 1 1 0 | 4.0 | 1 1 0 0 1 1 0 0 | 14.0 |
| 0 1 1 0 0 1 1 1 | 4.5 | 1 1 0 0 1 1 1 1 | 14.5 |
| 0 1 1 1 0 0 0 0 | 5.0 | 1 1 0 1 0 0 1 0 | 15.0 |
| 0 1 1 1 1 0 0 0 | 5.5 | 1 1 0 1 0 1 0 0 | 15.5 |
| 0 1 1 1 1 1 1 1 | 6.0 | 1 1 0 1 1 0 1 1 | 16.0 |
| 1 0 0 0 0 1 1 0 | 6.5 | 1 1 0 1 1 0 0 1 | 16.5 |
| 1 0 0 0 1 1 0 1 | 7.0 | 1 1 0 1 1 0 1 1 | 17.0 |
| 1 0 0 1 0 0 1 1 | 7.5 | 1 1 0 1 1 1 0 1 | 17.5 |
| 1 0 0 1 1 0 1 0 | 8.0 | 1 1 0 1 1 1 1 1 | 18.0 |
| 1 0 0 1 1 1 1 1 | 8.5 | 1 1 1 0 0 0 0 1 | 18.5 |
| 1 0 1 0 0 1 0 0 | 9.0 | 1 1 1 0 0 0 1 0 | 19.0 |
| 1 0 1 0 1 0 1 0 | 9.5 | 1 1 1 0 0 1 0 0 | 19.5 |
|  |  | 1 1 1 0 0 1 1 0 | 20.0 |

The counter-display shown in FIG. 9, uses logic devices coupled with 74188A, 32×8 bit programmable read-only memories 61, and decodes both 'coarse' and 'fine' data from the converter 29 to drive a 3×7 segment numerical display 62 which produces a read-out directly in dB. The 74188A programs are shown in Tables 2 and 3 below.

TABLE 2

Program for 74188A PROM: Chip display card

| Input | | | | | Output | | | | | | | |
|---|---|---|---|---|---|---|---|---|---|---|---|---|
| E | D | C | B | A | Y1 | Y2 | Y3 | Y4 | Y5 | Y6 | Y7 | Y8 |
| 0 | 0 | 0 | 0 | 0 | 1 | 1 | 1 | 1 | 1 | 1 | 0 | 0 |
| 0 | 0 | 0 | 0 | 1 | 0 | 1 | 1 | 0 | 0 | 0 | 0 | 0 |
| 0 | 0 | 0 | 1 | 0 | 1 | 1 | 0 | 1 | 1 | 0 | 1 | 0 |
| 0 | 0 | 0 | 1 | 1 | 1 | 1 | 1 | 1 | 0 | 0 | 1 | 0 |
| 0 | 0 | 1 | 0 | 0 | 0 | 1 | 1 | 0 | 0 | 1 | 1 | 0 |
| 0 | 0 | 1 | 0 | 1 | 1 | 0 | 1 | 1 | 0 | 1 | 1 | 0 |
| 0 | 0 | 1 | 1 | 0 | 0 | 0 | 1 | 1 | 1 | 1 | 1 | 0 |
| 0 | 0 | 1 | 1 | 1 | 1 | 1 | 1 | 0 | 0 | 0 | 0 | 0 |
| 0 | 1 | 0 | 0 | 0 | 1 | 1 | 1 | 1 | 1 | 1 | 1 | 1 |
| 0 | 1 | 0 | 0 | 1 | 1 | 1 | 1 | 0 | 0 | 1 | 1 | 0 |
| 0 | 1 | 0 | 1 | 0 | 1 | 1 | 1 | 1 | 1 | 0 | 0 | 0 |
| 0 | 1 | 0 | 1 | 1 | 0 | 1 | 1 | 0 | 0 | 0 | 0 | 0 |
| 0 | 1 | 1 | 0 | 0 | 1 | 1 | 0 | 1 | 1 | 0 | 1 | 0 |
| 0 | 1 | 1 | 0 | 1 | 1 | 1 | 1 | 1 | 0 | 0 | 1 | 0 |
| 0 | 1 | 1 | 1 | 0 | 0 | 1 | 1 | 0 | 0 | 1 | 1 | 0 |
| 0 | 1 | 1 | 1 | 1 | 1 | 0 | 1 | 1 | 0 | 1 | 1 | 0 |
| 1 | 0 | 0 | 0 | 0 | 0 | 0 | 1 | 1 | 1 | 1 | 1 | 0 |
| 1 | 0 | 0 | 0 | 1 | 1 | 1 | 1 | 0 | 0 | 0 | 0 | 0 |
| 1 | 0 | 0 | 1 | 0 | 1 | 1 | 1 | 1 | 1 | 1 | 1 | 0 |
| 1 | 0 | 0 | 1 | 1 | 1 | 1 | 1 | 0 | 0 | 1 | 1 | 0 |
| 1 | 0 | 1 | 0 | 0 | 1 | 1 | 1 | 1 | 1 | 1 | 0 | 0 |

TABLE 3

Program for 74188A PROM: Chip display card

| Input | | | | | Output | | | | | | | |
|---|---|---|---|---|---|---|---|---|---|---|---|---|
| E | D | C | B | A | Y1 | Y2 | Y3 | Y4 | Y5 | Y6 | Y7 | Y8 |
| 0 | 0 | 0 | 0 | 0 | 1 | 1 | 1 | 1 | 1 | 1 | 0 | 0 |
| 0 | 0 | 0 | 0 | 1 | 0 | 1 | 1 | 0 | 0 | 0 | 0 | 0 |
| 0 | 0 | 0 | 1 | 0 | 1 | 1 | 0 | 1 | 1 | 0 | 1 | 0 |
| 0 | 0 | 1 | 0 | 0 | 1 | 1 | 0 | 1 | 1 | 0 | 1 | 0 |
| 0 | 0 | 1 | 0 | 1 | 1 | 1 | 1 | 0 | 0 | 1 | 0 | 0 |
| 0 | 0 | 1 | 1 | 0 | 0 | 1 | 1 | 0 | 0 | 1 | 1 | 0 |
| 0 | 1 | 0 | 0 | 0 | 0 | 1 | 1 | 0 | 0 | 1 | 1 | 0 |
| 0 | 1 | 0 | 0 | 1 | 1 | 0 | 1 | 1 | 0 | 1 | 1 | 0 |

TABLE 3-continued

Program for 74188A PROM: Chip display card

| Input | | | | | Output | | | | | | | |
|---|---|---|---|---|---|---|---|---|---|---|---|---|
| E | D | C | B | A | Y1 | Y2 | Y3 | Y4 | Y5 | Y6 | Y7 | Y8 |
| 0 | 1 | 0 | 1 | 0 | 0 | 0 | 1 | 1 | 1 | 1 | 1 | 0 |
| 1 | 0 | 0 | 0 | 0 | 0 | 0 | 1 | 1 | 1 | 1 | 1 | 0 |
| 1 | 0 | 0 | 0 | 1 | 1 | 1 | 1 | 0 | 0 | 0 | 0 | 0 |
| 1 | 0 | 0 | 1 | 0 | 1 | 1 | 1 | 1 | 1 | 1 | 1 | 0 |
| 1 | 0 | 1 | 0 | 0 | 1 | 1 | 1 | 1 | 1 | 1 | 1 | 0 |
| 1 | 0 | 1 | 0 | 1 | 1 | 1 | 1 | 0 | 0 | 1 | 1 | 0 |
| 1 | 0 | 1 | 1 | 0 | 1 | 1 | 1 | 1 | 1 | 0 | 0 | 0 |

At normal pulse repetition rates the display would be updated at every pulse but this is too fast for an operator to read. A delay circuit 64 is incorporated so that an operator can select, using a binary switch 63, the required delay, which is dependent on the prf.

Delay settings are available from 10 to 90 in steps of 10, and from 100 to 900 in steps of 100. The delay circuit is designed so that the display generates a read-out for 1 pulse, ignoring the next (n−1) pulses, where n is the delay setting.

An undecoded output is available, carrying the information generated by every input pulse for more detailed processing if required.

A test/operate switch 65 is provided which overrides the delay circuitry permitting static testing of the memories and displays.

Figure 13:
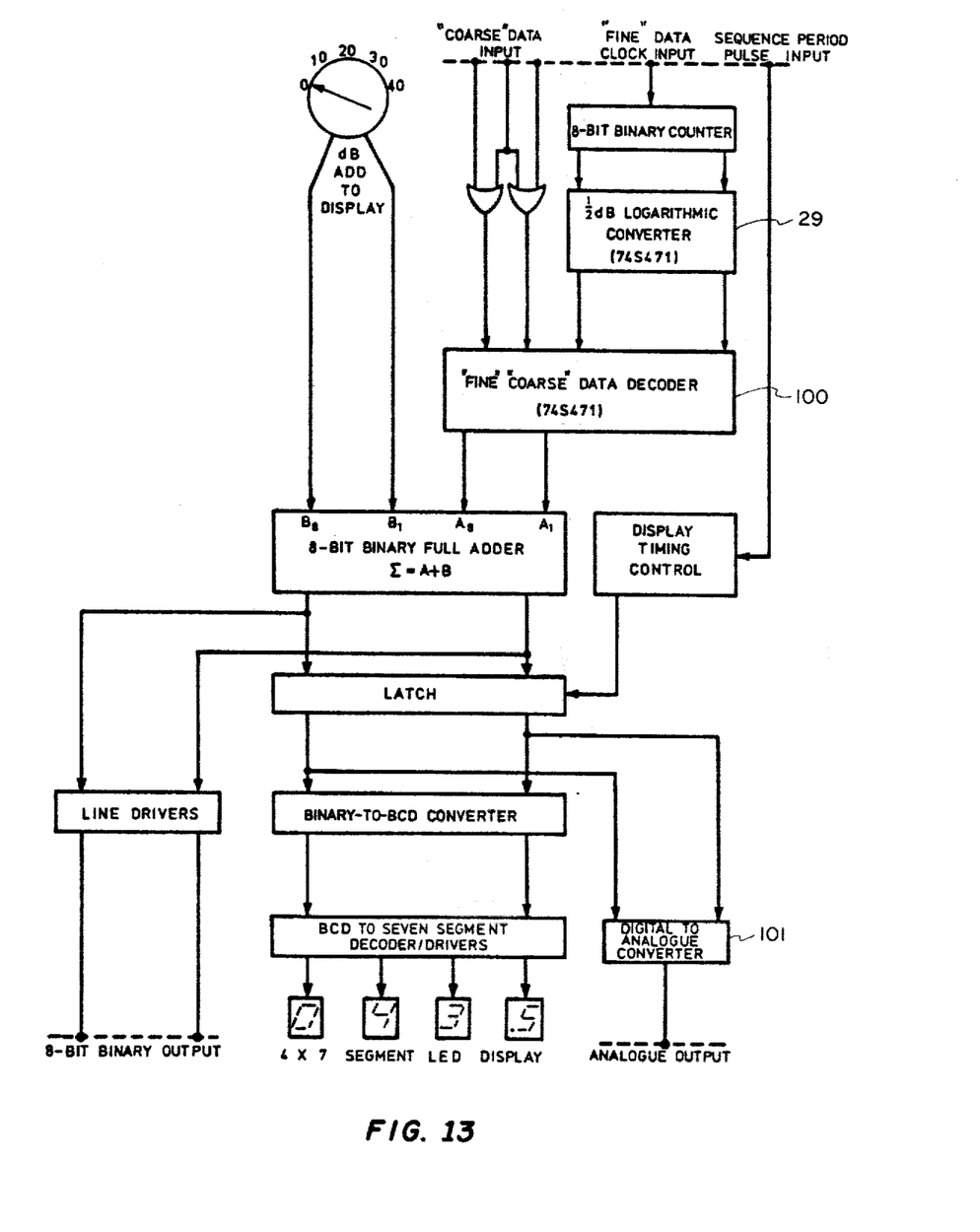
FIG. 13 is a block circuit diagram of part of a second auto-ranging ultrasonic attenuation meter in accordance with the invention.

Part of a second embodiment of the invention is shown in FIG. 13. This embodiment employs the same amplifiers, peak readers and comparators at the first embodiment described above but has the following modifications:

A single 256×8 bit prom 29, is used as a ½ dB logarithmic converter.

Data, giving 'coarse' and 'fine' attenuation levels is decoded by a second prom, 100, to generate a pure binary output to simplify interfacing with external equipment.

An external switch is provided to permit the addition of discrete binary levels to the output data and display. This allows the output reading range of the meter to be shifted from 0–80 dB to 40–120 dB in steps of 10 dB, and effects a change of reference point against which the attenuation measurements are made, and enables the operator to obtain readings which are the actual attenuation loss between the probes. Also a second DAC 101 may be added to generate an analog output voltage which is directly proportional to the attenuation. The analog level is updated at the same rate as the display.

What is claim is:

1. An autoranging ultrasonic attenuation meter comprising:
   receiver transducer means supplying an ultrasonic input signal,
   amplifier means for supplying a plurality of amplified input signals having different amplitude ranges,
   amplitude reader means for detecting and storing the peak voltage amplitudes of said input signal and amplified signals,
   comparator means for comparing the peak voltage of the signals with a constant reference voltage and to produce a binary output corresponding to each of said signals as a first quantisation of attenuation level,
   means supplying a reference voltage having constant and variable portions to said comparator means, means for selecting an output corresponding to one of said signals having a peak voltage in a predetermined range, and means for comparing the voltage of the selected output with said variable reference voltage to produce a second quantisation of attenuation level.

2. The device of claim 1 including means for summing said first and second quantisations in digital form to provide a total attenuation reading, and means for displaying said total attenuation reading.

3. The device of claim 2 including conversion means for producing the binary equivalent of the selected output as said second quantisation of attenuation level.

4. The device of claim 3 including means for decoding said first and second quantisations in digital form to produce a binary output equal to said total attenuation level.

5. The device of claim 3 wherein said means for selecting said output includes a timing and logic control circuit.

6. The device of claim 5 including a logarithmic converter supplying said second quantisation of attenuation level.

* * * * *